United States Patent [19]

Pogo et al.

[11] Patent Number: 5,683,696

[45] Date of Patent: Nov. 4, 1997

[54] CLONING OF DUFFY BLOOD GROUP ANTIGEN, GPD

[75] Inventors: Angel Oscar Pogo, Pelham; Asok Chaudhuri, Rego Park, both of N.Y.

[73] Assignee: New York Blood Center, Inc., New York, N.Y.

[21] Appl. No.: 486,670

[22] Filed: Jun. 7, 1995

Related U.S. Application Data

[62] Division of Ser. No. 140,797, Oct. 21, 1993, Pat. No. 5,578,714.

[51] Int. Cl.$^6$ .......................... C07K 14/705; A61K 38/00
[52] U.S. Cl. .......................... 424/185.1; 424/184.1; 435/69.3; 435/69.6; 435/71.1; 514/2; 514/12; 514/13; 530/300; 530/350; 530/380; 530/395
[58] Field of Search .......................... 530/350, 395, 530/380, 324–6; 424/185.1; 514/2, 12, 13; 435/69.3

[56] References Cited

U.S. PATENT DOCUMENTS 5,198,347  3/1993  Miller et al. .......................... 435/69.1
5,578,670  11/1996  Pogo et al. .......................... 536/23.5

OTHER PUBLICATIONS

Broome, S., et al., Biochemistry 75(6):2746–49 (Jun., 1978), "Immunological screening method to detect specific translation products".

Chaudhuri, A., et al., J. B.C. 264(23):13770–74 (1989), "Purification and characterization of an erythrocyte membrane protein complex carrying Duffy blood group antigenicity".

Chaudhuri, A., et al., Proc.Nat'l. Acad. Sci. 90:10793–97 (Nov., 1993), "Cloning of glycoprotein D cDNA, which encodes the major subunit of the Duffy blood group system and the receptor for the Plasmodium vivax malaria parasite".

Goodman, H. M., et al., Methods in Enzymology, vol. 68, pp. 75–90 (1979), "Cloning of hormone genes from a mixture of cDNA molecules".

Nichols, M. E., et al., J. Exp. Med. 166:776–785 (Sep., 1988), "A new human Duffy blood group specificity defined by a murine monoclonal antibody".

*Primary Examiner*—Thomas M. Cunningham
*Attorney, Agent, or Firm*—Sprung Kramer Schaefer & Briscoe

[57] ABSTRACT gpD protein, the major subunit of the Duffy blood group antigenic system, has been isolated. gpD protein contains the receptor, by which *P. vivax* enters red cells and causes malaria. gpD has significant sequence homology with human and rabbit interleukin-8 receptors and, therefore, gpD protein likely is a new class of chemoattractant cytokines receptor. gpD protein cDNA has a quasi-total homology with a human hippocampus cDNA clone HHCMF86 and, therefore, gpD protein or a homologous protein may be present as a neuropeptide receptor in brain. gpD protein is present in all red cell progenitors and it may be a receptor for cell proliferation and/or differentiation. gpD protein cDNA identifies in human kidney a mRNA of the same size as the bone marrow. Since the kidney is not and has no potential to become an erythropoietic organ, this putative chemoattractant receptor may have essential renal functions. gpD protein has therapeutic value in the prevention of malaria and in the regulation of erythrocyte, neural and renal functions and can be combined with physiologically acceptable diluents to yield a therapeutic agent suitable for these purposes. Peptides corresponding to a portion of gpD protein that contains the receptor also have been synthesized. Such peptides have therapeutic usefulness identical to that of gpD protein. gpD protein and such peptides also have utility in the production of therapeutics, e.g., antibodies, complementary peptides, etc., which are also useful to treat malaria and regulate essential erythrocyte, neural and renal functions.

18 Claims, 7 Drawing Sheets

FIG. 1B-1

```
                                                                                              55
  1    G GCT TCC CCA GGA CTG TTC CTG CTC CCT GCT TTG TCC TTT
         A   S   P   G   L   F   L   L   P   A   L   S   F 112
 18    TCC ACT GTC CGC ACT GCA TCT GAC TCC TGC AGA GAC CTT CCA GAC CTT
         S   T   V   R   T   A   S   D   S   C   R   D   L   P   D   L 169
 37    CCT CTC TGT CCT CCC CTC CCA CCT GCC CCT CAG CTT GTT CTC CCA GAC
         P   L   C   P   P   L   P   P   A   P   Q   L   V   L   P   D 226
 56    ACT CTG ATG GCC TCT GGG TAT GAG CTT CCA GGA GAC TTC CCA GGA GTC
         T   L   M   A   S   G   Y   E   L   P   G   D   F   P   G   V 283
 75    AAC TCA AGT CAG CTG GAC TTC GAA GAT CCT CAG CAG GCG GAG TCC TCA
         N   S   S   Q   L   D   F   E   D   P   Q   Q   A   E   S   S 340
 94    TCC TTC CCA GAT GGA GAC TAT GAT GGA AAT TCT TGG AAT GTA TAT GGT
         S   F   P   D   G   D   Y   D   G   N   S   W   N   V   Y   G 397
113    TGT AAC TGT CTG GAT GAC TCT GCA GCA GAA AAC GCC CTG CCC TCC AAT
         C   N   C   L   D   D   S   A   A   E   N   A   L   P   S   N 454
132    ATC CTA GCT AGC AGC ACT GTC CTC CTG TTC TTC ATC CTC TGC CAC
         I   L   A   S   S   T   V   L   L   F   F   I   L   C   H

511
         CTC TGC CCT CTT TGG CCT GTC CTG CTT ATG CTT CTT AGA AGA GCT GTC CGC
          L   C   P   L   W   P   V   L   L   M   L   F   R   R   A   V   R
                  |____Pe 1____|                                     |____Pe 1____|

568
         ATT GTG GTG CCC GTC CTT GCC CCA GTG GCA GGG CTA GGT AGC AGT GTC CTG GGT G
          I   V   V   P   V   L   A   P   V   A   G   L   G   S   S   V   L   G
           |____Pe 2____|                                                 |____Pe 2____|

625
         AGC CTG GGC TAC TGT GTC TGG TAT GGC TTT GCC CAG GCT TTG CTG CTA GGG
          S   L   G   Y   C   V   W   Y   G   F   A   Q   A   L   L   L   G
                                              |____Pe 3____|
```

FIG. 1B-2

```
151  TGC CAT GCC TCC CTG GGC CAC AGA CTG GGT GCA GGC CAG GTC CCA GGC CTC ACC CTG  682
     C   H   A   S   L   G   H   R   L   G   A   G   Q   V   P   G   L   T   L
170  GGG CTC ACT GTG GGA ATT TGG GGA GTG GTG CTA ACA CTG CCT GTC ACC CTG           739
     G   L   T   V   G   I   W   G   V   V   L   T   L   P   V   T   L
              Pe 4
189  GCC AGT GGT GCT TCT GGT GGA CTC TGC GCC CTA ATA TAC AGC ACG GAG AAG CTG GCT   796
     A   S   G   A   S   G   G   L   C   A   L   I   Y   S   T   E   K   L   A
208  TTG CAG GCC ACA CAC ACT GTA GCC CTG CTT TGT CTT TTT GTC TTG CCA TTG GGT        853
     L   Q   A   T   H   T   V   A   L   L   C   L   F   V   L   P   L   G
227  TTG TTT GGA GCC AAG GGG AAG CTG GCA TTG GGT ATG GGG CCA CCC CCC TGG ATG        910
     L   F   G   A   K   G   K   L   A   L   G   M   G   P   P   P   W   M
246  AAT ATC CTG TGG GCC TGG TTT ATT TTC TGG CCT CAT GGG GTG CTA GGA CTG            967
     H   I   L   W   A   W   F   I   F   W   P   H   G   V   L   G   L
              Pe 5
265  GAT TTC CTG GTG AGG TCC AAG CTG TTG CTG TTG TCA ACA TGT CTG GCC CAG GCT       1024
     D   F   L   V   R   S   K   L   L   L   L   S   T   C   L   A   Q   A
        Pe 5
284  CTG GAC CTG CTG AAC CTG CTG GCA GAA CTG GCC ATT TTG CAC TGT GTG GCT ACG       1081
     L   D   L   L   N   L   L   A   E   L   A   I   L   H   C   V   A   T
303  CCC CTG CTC CTC GCC CTA TTC TGC CAC CAG CGC ACC CTT CTC TTG CCC TCT CTG       1138
     P   L   L   L   A   L   F   C   H   Q   R   T   L   L   L   P   S   L
322  CCC CTC CCT GAA GGA TGG TCT CAT CTG AAA GTC TAC ACT GCC TTT GTG AGC AAA AAA TCC TAG TTC  1195
     P   L   P   E   G   W   S   H   L   K   V   Y   T   A   F   V   S   K   S   *
        Pe 6                              Pe 6
     TCT TCC CAC CTG TCA ACC TGA ATT AAA GTC TAC ACT GCC TTT GTG AAA AAA AAA AAA  1252
     AAA AAA AAA AAA AAA                                                          1267
```

```
              334       343       353       363       373       383       393
GPD PROTEIN   CCACTCCTGTAACCTGCTGGATGACTCTGCACTGCCCTTCTTCATCCTCACCAGTGTCCT
              ||||||||||||||||||||||||||||||||||||||||||||||||||||||||||||
HHCMF86       CCACTCCTGTAACCTGCTGGATGACTCTGCACTGCCCTTCTTCATCCTCACCAGTGTCCT
              1         10        20        30        40        50        60

394       403       413       423       433       443       453
GPD PROTEIN   GGGTATCCTAGCTAGCAGCACTGTCCTCTTCATGCTTTTCAGACCTCTCTTCCGCTGGCA
              |||||||||||||||||||||||||||||||||||||| |||||||||||||||||||||
HHCMF86       GGGTATCCTAGCTAGCAGCACTGTCCTCTTCATGCTTTTNAGACCTCTCTTCCGCTGGCA
              61        70        80        90        100       110       120

454       463       473       483       493       503       513
GPD PROTEIN   GCTCTGCCCTGGCTGGCCTGTCCTGGCACAGCTGGCTGTGGGCAGTGCCCTCTTCAGCAT
              ||||||||||||||||||||||||||||||||||||||||||||||||||||||||||||
HHCMF86       GCTCTGCCCTGGCTGGCCTGTCCTGGCACAGCTGGCTGTGGGCAGTGCCCTCTTCAGCAT
              121       130       140       150       160       170       180

514       523       533       543       553       563       573
GPD PROTEIN   TGTGGTGCCCGTCTTGGCCCCAGGGCTAGGTAGCACTCGCAGCTCTGCCCTGTGTAGCCT
              |||||||||||| |||||||||||||||||||||||||||||||||||||||||||||||
HHCMF86       TGTGGTGCCCGTTTTGGCCCCAGGGCTAGGTAGCACTCGCAGCTCTGCCCTGTGTAGCCT
              181       190       200       210       220       230       240

574       583       593       603       613       623       633
GPD PROTEIN   GGCTACTGTGTCTGGTATGGCTCAGCCTTTGCCCAGGCTTTGCTGCTA-GGGTGCCATG
              ||||||||||||||||||||||||||| ||||||| ||||||||||||| |||||||||
HHCMF86       GGGCTACTGTGTCTGGTATGGCTCAGCCTTTGNCCAGGCTTTGCTGCTAAGGGTGCCATG
              241       250       260       270       280       290       300

634       643       653       663       673       683       693
GPD PROTEIN   CCTCCCTGGGCCACAGACTGGGTGCAGGCCAGGTCCCAGGCCTCACCCTGGGGCTCACTG
              |||||||||| ||||||||||||||||||
HHCMF86       CCTCCCTGGGNCACAGACTGGGTGCAGG.............................
              301       310       320       330       340       350       360

694
GPD PROTEIN   TGGGAATT

HHCMF86       ........
              361
```

MATCHING PERCENTAGE

TOTAL WINDOW        87%  ( 323/ 368)

ALIGNMENT WINDOW    98%  ( 323/ 328)

FIG. 5

CLONING OF DUFFY BLOOD GROUP ANTIGEN, GPD

This application is a divisional, of application Ser. No. 08/140,797, filed Oct. 21, 1993, now U.S. Pat. No. 5,578,714.

BACKGROUND OF THE INVENTION

1. Field of the Invention

The present invention relates to the gpD protein, which is the major subunit of the Duffy blood group antigen, and the use thereof in the detection and treatment of malaria.

2. Description of the Related Art

Malaria is the most prevalent infectious disease of mankind. Its widespread geographic distribution together with the severe pathologic consequences of the infection make malaria a major medical and financial burden for many of the developing nations.

There are several different kinds of malaria, one of which is caused by the parasite *Plasmodium vivax*, which attacks the red blood cells of susceptible individuals. A genetic trait of special interest with regard to *P. vivax* is the absence of antigen encoded by the blood group system called Duffy (F. B. Livingston, "The Duffy Blood Groups, Vivax Malaria and Malaria Sections in Human Populations: Review", *Human Biol.*, 56, 413, (1984)). It has been shown that individuals whose red blood cells lack the product of the Duffy genes are not susceptible to the penetration of *P. vivax* owing to the fact that Duffy molecules serve as the receptor for the parasite. (L. H. Miller, H. J. Mason, D. F. Clyde and M. H. McGinnis, "The Resistance Factor to *Plasmodium Vivax* in Blacks, The Duffy Blood Group Genotype (a−b−)", *N. Eng. J. Med.*, 295, 302, (1976)).

Malarial parasites are transmitted from host to host by blood sucking females of several species of the genus Anopheles. It is in the mosquito that the sexual phase of the life cycle of *P. vivax* takes place leading to the production of sporozoites. After their introduction into a "new" host, these sporozoites reside in the parenchymal cells of the liver and multiply asexually causing the eventual rupture of hepatic cells and the release of asexual forms (merozoites) into the blood stream. There the merozoites actively penetrate into red blood cells in a nearly synchronous fashion and because the rate of growth and cell division of *P. vivax* is essentially identical, the infected erythrocytes simultaneously reach the stage of parasite load at which they break. This produces the typical cycles of fever every 48 hours, hence the name of *Tertian malaria*.

*P. vivax* infection may persist without treatment for as long as five years. *P. vivax* parasitemias are relatively low-grade, primarily because the parasites favor the few young red blood cells or reticulocytes that exist in peripheral blood.

Immunity to *P. vivax* is commonly only partial in nature, which allows the occurrence of superinfections that evolve independently causing an overlap in the cycles of parasite release leading to the appearance of fever in shorter cycles. *P. vivax* exhibits considerable antigenic diversity and variation, as do other malarial Plasmodia (M. Hommel, Antigenic Variation in Malaria Parasites", *Immunology Today*, 6, 28, (1985)), although it has been recently shown that antigenic components of *P. vivax* sporozoites exist that are common to parasites from different isolates (F. Zavala, A. Masuda, P. M. Graves, V. Nussenzweig and R. Nussenzweig, "Ubiquity of the Repetitive Epitope of the CS Protein in Different Isolates of Human Malaria-Parasites", *J. Immunol.*, 135, 2790, (1985)).

In the context of the sources of antigenic differences between *P. vivax* isolates and their consequences with regard to vaccination, it is important that the merozoites of different strains of *P. vivax* share the same receptor for penetration into red blood cells, i.e., the Duffy molecule (Miller. et al., *N. Engl. J. Med.*, supra). In addition, regardless of its capacity to vary other antigenic molecules, the parasite recognition molecule, i.e., the molecule that binds to the Duffy molecule, must remain constant since it is the complementarity between it and the invariant receptor that allows the penetration of merozoites into erythrocytes and, thus, the continuity of the infection. Changes in the ligand specificity of this molecule would result in the loss of the parasite's capacity to infect, since *P. vivax* merozoites appear to be unable to utilize other human red blood cell receptors for their penetration in vivo, as shown by the resistance of Duffy negative erythrocytes.

The Duffy blood group system consists of two principal antigens $Fy^a$ and $Fy^b$ produced by $Fy^a$ and $Fy^b$ alleles. Antisera anti-$Fy^a$ and anti-$Fy^b$ defined four phenotypes, Fy(a+b−), Fy(a−b+), Fy(a+b+) and Fy(a−b−). W. L. Marsh, *Crit. Rev. Clin. Lab. Sci.*, 5, 387 (1975). Neither antiserum agglutinates Duffy Fy(a−b−) cells, the predominate phenotype in blacks. Antisera defining the other phenotypes, Fy3, Fy4 and Fy5, are very rare. A murine monoclonal antibody, anti-Fy6, defined a new Duffy antigenic determinant present in all Duffy positive cells but absent in Fy(a−b−) cells. M. E. Nichols, P. Rubinstein, J. Barnwell, S. R. de Cordoba, and R. E. Rosenfield, *J. Exp. Med.*, 166, 776 (1987). Blacks with Fy(a−b−) erythrocytes cannot be infected by *P. vivax*. These cells are also resistant to the in vitro invasion by *P. knowlesi*, a simian parasite that invades Fy(a+b−) and Fy(a−b+) human erythrocytes. L. H. Miller, S. J. Mason, J. A. Dvorak, M. H. McGinniss and K. I. Rothman, *Science*, 189, 561 (1985). Receptors for red cell invasion by these parasites, therefore, are related to the Duffy blood group system.

DEFINITIONS

The following amino acids may be indicated by the following 3- or 1-letter codes elsewhere in the specification:

| Amino Acid | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

SUMMARY OF THE INVENTION

Using an anti-Fy6 monoclonal antibody, there has now been developed a procedure for purification of Duffy antigens in human red cells. Duffy antigens appear to be multimeric red cell membrane proteins composed of different subunits. A glycoprotein, named gpD, of a molecular mass of 35–45 kDa, is the major subunit of the protein complex, and has the antigenic determinants defined by anti-Fy$^a$, anti-Fy$^b$, and anti-Fy6 antibodies. The characterization, at the molecular level, of this novel protein is crucial in finding its function on the red cell membrane, in understanding the parasite-erythrocyte recognition process, and in resolving the molecular mechanism of parasite invasion. The present invention relates to the isolation, sequence analysis and tissue expression of a mRNA encoding the gpD protein.

gpD protein has significant sequence homology with human and rabbit interleukin-8 receptors and, therefore, gpD protein most probably is a new class of chemoattractant cytokines receptor. Also, gpD protein cDNA has a quasi-total homology with a human hippocampus cDNA clone HHCMF86 and, therefore, it is highly probable that gpD protein or a homologous protein is present as a neuropeptide receptor in brain. gpD is present in all red cell progenitors and the possibility exists that it may function as a receptor for cell proliferation and/or differentiation. gpD protein cDNA identifies in human kidney a mRNA of the same size as the bone marrow. Since the kidney is not and has no potential to become an erythropoietic organ, it is possible that this putative chemoattractant receptor has essential renal functions.

gpD protein has therapeutic value in the prevention of malaria and in the regulation of essential erythrocyte, neural and renal functions and can be combined with physiologically acceptable diluents to yield a therapeutic agent suitable for these purposes.

Peptides corresponding to a portion of gpD protein that contains the receptor also have been synthesized. Such peptides have therapeutic usefulness identical to that of gpD protein itself and, as is the case with gpD protein, the synthetic peptides can be combined with physiologically acceptable diluents to yield a vaccine against malaria or a therapeutic agent useful to regulate essential erythrocyte, neural and renal functions.

gpD protein and synthetic peptides corresponding to a portion of gpD protein also have utility in the production of therapeutics, e.g., antibodies, complementary peptides, and drugs modeled on the tertiary structure of the gpD protein or synthetic peptides, which are also of therapeutic value in the treatment of malaria and in the regulation of essential erythrocyte, neural and renal functions.

BRIEF DESCRIPTION OF THE DRAWINGS

The invention will now be described in detail with reference to the drawings, wherein:

FIG. 1b is the schematic of the nucleotide and amino acid sequences of the combined Fyb71–81 cDNA clones encoding gpD protein.

FIG. 5 is a chart showing the DNA sequence homology between gpD protein and hippocampus cDNA clone HHCMF86.

DETAILED DESCRIPTION OF THE INVENTION

Figure 1A:
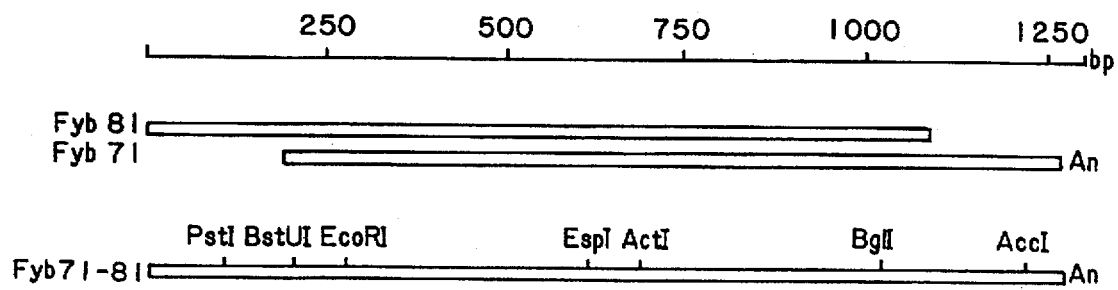
FIG. 1a is the schematic representation and partial restriction map of the two longest gpD protein cDNA clones.

Four cDNA clones that encode gpD protein, the major subunit of the Duffy blood group antigenic system, have been isolated. From these four cDNA clones, the nucleotide sequence of a structural gene encoding gpD protein has been determined. The sequence is shown in FIG. 1 and is designated SEQ ID No: 1. Due to the degeneracy of the genetic code, there may exist other natural DNA sequences that encode the identical gpD protein. The present invention, therefore, extends to such other natural DNA sequences as well as to synthetic DNA sequences having the same DNA sequence as shown in SEQ ID No: 1 and such other natural DNA sequences. The synthesis of DNA can be by any conventional means.

FIG. 1 also shows the amino acid sequence of gpD protein. As was the case with respect to the DNA sequence of the structural gene, the present invention extends to gpD isolated from natural sources or to gpD prepared by chemical synthesis. The chemical synthesis can be by any conventional means.

In FIG. 1, amino acid residues are numbered on the left; nucleotide positions are numbered on the right. The positions of peptides that match predicted amino acids, are shown by solid single lines. The two potential carbohydrate binding sites to asparagine residues, are shown by up arrows. The third glycosylation site, the asparagine at position 37, is unlikely to occur since it is followed by aspartic acid. See R. D. Marshall, Annu. Rev. Biochem., 41, 673 (1972). Double underline at the 5' end is the sequence used to primer extend the 5' end, and at the 3' end is the consensus poly(A) addition sequence.

gpD protein is a highly hydrophobic intramembrane glycoprotein with nine putative transmembrane α-helices. The cognate gene is present in Duffy positive and negative individuals, but the bone marrow of Duffy negative individuals does not synthesize gpD specific mRNA. In adult kidney, spleen and fetal liver, the mRNA has the same size as gpD mRNA; however, in brain, the mRNA is much larger. The clones that have been characterized will provide the elements to investigate: (i) the structural components of gpD genes, (ii) the biosynthesis and expression of gpD protein in human bone marrow and other tissues, (iii) the structure-function of this novel red cell membrane protein that might exist in other cell types and may function as a chemokine receptor, and (iv) the role of gpD protein as the receptor for P. vivax merozoite invasion.

P. Rubinstein et al., U.S. Pat. No. 5,101,017, have disclosed a monoclonal antibody specific for gpD protein (hereinafter "the Rubinstein antibody"). The Rubinstein antibody blocks the penetration of the P. vivax malaria parasite into human red blood cells by virtue of effective blocking of the target molecule of the P. vivax malaria parasite. It is likely that the Rubinstein antibody has a combining site that has the same stereochemistry as the ligand site on P. vivax, and elicits anti-idiotypic antibodies that react with the parasite. As a result of these properties, the Rubinstein antibody is useful, for example, for the immunodiagnosis of P. vivax infection, to induce anti-idiotypic responses, as alluded to above, that protect against these parasites, and directly in vivo to block the red cell receptors for the parasites. Details of these and other uses of the Rubinstein et al. antibody are disclosed in the patent, the entire contents of which are hereby incorporated by reference.

The Rubinstein antibody was prepared essentially by the method of G. Kohler and C. Milstein (*Nature*, 256, 495 (1975)). Mice were immunized with human red cells of the Fy(a+b+) type, the spleen removed and hybridized with a suspension of mouse myeloma cell line P3/NSO-Ag4-1 (NS-O) (obtained from the ATCC (American Type Culture Collection, Rockville, Md.)), and the hybridomas tested for the secretion of antibodies that bound to human red cells. One well was found to contain antibodies that bound to erythrocytes of the Fy(a+b−) and Fy(a−b+) types, but not to erythrocytes of the Fy(a−b−) type. The cellular contents of that well were recovered, subjected to dilution and cloned. One of the clones was found to secrete the Rubinstein antibody.

As noted above, the Rubinstein antibody is specific for the gpD protein, now cloned. Accordingly, the inventive gpD protein is also useful to prepare monoclonal antibodies having the same specificity as the Rubinstein antibody. The procedure for preparing such antibodies is essentially the same procedure that Rubinstein et al. employed except that instead of immunizing mice with human red cells, immunization is with gpD protein.

Additionally, the N-terminal (exocellular) region of the gpD protein has been identified as being involved in the interaction of the malaria parasite with the red cell. Work is currently ongoing with synthetic peptides to identify the precise amino acid residues involved in this interaction. The following peptides have been found to bind the Rubinstein antibody in an ELISA assay:

(1) MASSGYVLQAELSPSTENSSQLDFEDVWNSSYGVNDSFPDGDYDANLEAAAPCHSCNLLDDSALPF, which has been designated SEQ ID No: 8;

(2) MASSGYVLQAELSPSTENSSQLDFEDVWNSSYGVNDSFPDGDYD, which has been designated SEQ ID No: 9; and (3) AELSPSTENSSQLDFEDVWNSSYGVNDSFPDGDYD, which has been designated SEQ ID No: 10.

The following peptides do not bind to the Rubinstein antibody in an ELISA assay:

(4) DFEDVWNSSYGVNDSFPDGDYD, which has been designated SEQ ID No: 11;

(5) ANLEAAAPCHSCNLLDDSALPF, which has been designated SEQ ID No: 12; and (6) AELSPSTENSSQL, which has been designated SEQ ID No: 13.

The fact that peptide (3) binds the Rubinstein antibody whereas peptides (4) and (6) do not suggests that the junction between the C-terminal of peptide (6) and the N-terminal of peptide (4) is important for binding. The amino acid sequence AELSPSTENSSQLDFEDVWNSS, which has been designated SEQ ID No: 14, likely contains the epitope for the Rubinstein antibody. Therefore, the invention also extends to peptides comprising the amino acid sequence depicted in SEQ ID No: 14.

The peptides designated SEQ ID No: 8, SEQ ID No: 9, SEQ ID No: 10, and SEQ ID No: 14, as well as peptides containing SEQ ID No: 14, bind the parasite in vivo and, therefore, can be used as the immunogen in a vaccine against malaria. The present invention is, consequently, also directed to such vaccines as well as to a method of protecting a warm-blooded animal, especially, a human, against infection by *P. vivax* by administering to such animal an effective amount of said immunogen. Since synthetic peptides are typically poor immunogens, it may be advantageous to conjugate the peptides to a carrier, e.g., a protein carrier such as tetanus toxoid, keyhole lympet hemocyanin (KLH), etc., or a lipid carrier such as those taught by R. Neurath et al. in U.S. Pat. Nos. 4,847,080 and 5,204,096, the disclosures of which are hereby incorporated by reference, or by T. Hoppe in U.S. Pat. No. 5,019,383, the disclosure of which is also hereby incorporated by reference.

The inventive peptides can be formed from natural sources, i.e., by proteolytic cleavage of gpD protein, or through chemical synthesis. Details on chemical synthesis of peptides and linkage of peptides to carriers can be found in U.S. Pat. Nos. 4,847,080 and 5,204,096.

In the inventive vaccines, the inventive peptides will usually be present along with a physiologically acceptable diluent (medium), e.g., phosphate buffered saline containing an adjuvant. Generally speaking, the amount of the peptide in the physiologically acceptable diluent will be between approximately 1 µg and 1 mg per dose.

A suitable vaccine can also be formulated using gpD protein in similar amounts in similar diluents, although for most applications the use of synthetic peptides will be more practical.

In either case, the inventive vaccine can be administered by subcutaneous, intravenous, intradermal or intramuscular injection. While the preferred route would depend upon the particular vaccine, intramuscular injection will be generally suitable. Frequency of administration will vary depending on the vaccine.

It is known, for example, from J. H. Adams et al., *Proc. Natl. Acad. Sci. USA*, 89, 7085 (1992), that the binding regions identified in all Plasmodium malaria proteins are homologous. Therefore, gpD protein and the inventive peptides bind to and interfere with the erythrocyte binding of all Plasmodia. This means that the inventive vaccine will be generally useful against all types of malaria and the invention, thus, extends to a method of protecting a warm-blooded animal against malaria due to any Plasmodia.

gpD protein shows significant homology to interleukin-8 (IL-8) receptors on erythrocytes. This is consistent with a recent report suggesting that the Duffy blood group antigen and the erythrocyte chemokine receptor are the same protein. R. Horuk et al., "A Receptor for the Malarial Parasite *Plasmodium vivax*: The Erythrocyte Chemokine Receptor", *Science*, 261, 1182 (1993). The erythrocyte receptor apparently differs from the IL-8 receptors, IL-8RA and IL-8RB on neutrophils. The erythrocyte receptor binds a family of chemotactic and proinflammatory soluble peptides, including IL-8, melanoma growth stimulatory activity (MGSA), monocyte chemotactic protein 1 (MCP-1), and regulated on activation, normal T expressed and secreted (RANTES) protein. Administration of gpD protein (or the inventive synthetic peptides) interferes with the normal binding of these proteins to the erythrocyte receptor and, consequently, is useful to regulate the physiological effects of the secretion of these proteins. For example, it has been postulated that the erythrocyte receptor acts as a scavenger for certain inflammatory mediators, including IL-8. Administration of gpD protein (or the inventive synthetic peptides), therefore, would be expected to enhance scavenging of IL-8, thereby, lessening any IL-8 induced inflammation. For this purpose, the inventive vaccine, as described above, is suitable as a therapeutic agent.

gpD protein also shows significant homology to a human hippocampus cDNA clone HHCMF86 and, therefore, it is highly probable that gpD protein or a homologous protein is present as a neuropeptide receptor in brain. gpD protein cDNA identifies in human kidney with a mRNA of the same size as the bone marrow and, therefore, gpD protein or a homologous protein plays some role in the regulation of renal function. The inventive therapeutic agent will, accordingly, also find use in the regulation of these neural and renal functions.

Proteins that are complementary to gpD protein or the inventive synthetic peptides, e.g., antibodies specific to gpD, will block the natural receptor(s) and, consequently, will also have the therapeutic utilities outlined above. In the preparation of such complementary proteins, the use of gpD protein or the inventive synthetic peptides are of obvious value.

The invention will be further described with reference to the following non-limiting examples.

Example 1

Partial Amino Acid Sequence Analysis of gpD protein

Red cells (Fy(a-b+)) were washed three times in cold phosphate-buffered saline (PBS) (pH 7.4), resuspended in the same solution, and mixed continuously overnight at 4° C. with the Rubinstein antibody at a concentration of 10 μg/ml of packed red cells. (This concentration determined with radioiodinated antibody, exceeds the concentration required to saturate Duffy antigen sites.) Unbound antibody was removed by washing the red cells with cold PBS. Red cell ghosts were prepared by hypotonic lysis with 20 volumes of cold 5 mM sodium phosphate buffer (pH 7.4) containing 1 mM phenylmethylsulfonyl fluoride and 100 kallikrein-inactivating units/ml Trasylol™ (aprotinin). Then the ghosts were washed exhaustively until they were light pink in color. Ghosts were centrifuged for 30 min at 43,000× g; supernatant was decanted, and the pellet was made to 50 mM Hepes-NaOH, pH 8.0, 1 mM phenylmethylsulfonyl fluoride, 100 kallikrein-inactivating units/ml Trasylol, and frozen at -20° C.

Frozen ghosts were later thawed and centrifuged for 30 min at 43,000×g. The pellet was resuspended in 50 mM Hepes-NaOH, pH 8.0, 1 mM phenylmethylsulfonyl fluoride, 100 kallikrein-inactivating units/ml Trasylol to three times the initial volume of packed red cells. Triton X-100™ (peroxide free) detergent was added to a final concentration of 1%, and the solution was mixed gently for 1 h at room temperature. Shells were removed by centrifugation for 30 min at 43,000×g. The supernatant was concentrated 4-fold in an Amicon concentrator using a PM Y10 filter (Amicon Corp.) under nitrogen pressure.

A 0.1 volume of PBS solution, 10 times the normal concentration, was added to the detergent extract. The detergent extract was then incubated with Sepharose 4B™ beads coupled to anti-mouse IgG for 1 h at room temperature. The ratio of beads to detergent extract was 1:100 (v/v). The anti-mouse IgG-Sepharose beads were removed by centrifugation, and washed in a solution containing PBS and 0.5% Triton X-100 at a 1:20 (v/v) ratio of beads to washing solution. The washings were done at room temperature and repeated three times. Elution was done by incubating the beads in a solution containing 62.5 mM Tris-HCl (pH 6.8), 0.5% sodium dodecyl sulfate (SDS) at a 1:2 (v/v) ratio beads to eluant. The incubation was at 65° C. for 10 min and repeated three times. The eluted material was concentrated in an Amicon concentrator with PM Y10™ filter (Amicon Corp.) under nitrogen pressure.

Polyacrylamide gel electrophoresis (PAGE) in the presence of 0.1% SDS was performed according to U. K. Laemmli, Nature, 227, 680 (1970), with the following modifications: the acrylamide concentration was 10%, polymerization was done overnight to destroy oxidizing reagents, and 0.1 mM thioglycolate was added in the upper chamber. To the concentrated solution of affinity purified material, the following chemicals were added: urea to 4M, SDS to 2%, and β-mercapoethanol to 5%. After electrophoresis, the gels were fixed for 30 min in 10% isoamyl alcohol and 5% acetic acid and stained with 0.002% Coomassie Blue R-250 until marker protein bands were seen. Regions that corresponded between the 36–46 kDa region and above the 96 kDa region were excused, destained with several changes of 5% acetic acid, and washed with distilled water. Gel pieces were stored at -20° C. or used immediately.

Gel pieces, cut into 4×4 mm cubes were delivered into the elution chamber of an Elutrap™ apparatus (Schleicher and Schuell) and eluted overnight in 50 mM ammonium bicarbonate, 0.1% SDS solution at 100 volts (constant). Fresh 50 mM ammonium bicarbonate, 0.1% SDS solution was added, and electroelution was continued for an additional 6–8 h. Eluted material was concentrated by Centricon™ microconcentrator (Amicon Corp.).

The purified protein was alkylated and cleaved with cyanogen bromide (CNBr) as follows: The purified protein was precipitated with cold acetone in the presence of 1 mM HCl at -20° C. for 2 hours. Precipitate was washed with 100% cold acetone, evaporated to dryness at room temperature and was dissolved in 0.1M Tris-HCl, pH 8.0 plus 0.5% SDS. Solid DTT was added to the solution to make final DTT concentration of 10 mg/ml and the solution was reduced for 2 hours at 85° C. One tenth volume of 2.68M Iodoacetic acetamide was added to the solution and the tube was flushed with nitrogen, incubated for 30 minutes at room temperature in the dark. After incubation, solid DTT was added to 10 mg/ml and dialyzed overnight against 0.1M Tris-HCl (pH 8.0) plus 0.5% SDS. Protein was precipitated with acetone as above and air dried. Precipitate was dissolved in 96 μl of 70% formic acid and 4 μl of 1M CNBr solution in 70% formic acid and incubated at room temperature for 48 hours in the dark. Acid was evaporated to dryness and the pellet was washed with water and evaporated to dryness for several times. The digested protein was subjected to either high performance liquid chromatography (HPLC) or polyacrylamide gel fractionation.

Pe 1 peptide was obtained by sequencing the non-fractionated CNBr digest using the O-phthalaldehyde (OPA) blocking reagent (see, A. W. Brauer et al., Anal. Biochem., 137, 134 (1983)). Pe 5 peptide was the partial sequence of the only fragment (~4 kDa) that separated very well from the CNBr digest run of the three layer SDS-PAGE system (see, H. Shagger et al., Anal. Biochem., 168, 368 (1987)). After the run, the peptide fragment was electroblotted onto ProBlott™ (Applied Biosystems) and sequenced (see, N. LeGendre et al., A Practical Guide to Protein and Peptide Purification for Microsequencing, P. T. Matsudaira, ed., (Academic Press, New York), 49–69 (1989)). Another aliquot was digested with pepsin (5/1 ratio) at 37° C. overnight and the fragments were separated by reverse-phase HPLC using Vydac C-18 column. Pe 2, Pe 3, Pe 4 and Pe 6 peptides, which eluted as single peaks from a reverse-phase HPLC column and were the few pepsin peptides yielded by reverse-phase HPLC, were sequenced. Applied Biosystems Protein/Peptide Sequencer™, Model 470 or 477, was used according to the manufacturer's recommendations. Pepsin digestions at 10/1 ratio and 4° C. for 30 or 60 min, did not generate larger peptides.

Example 2

Primer Design and Polymerase Chain Reaction (PCR)

Pe 5 was the most promising for generating a probe for the selection of gpD protein clones. Pe 2, Pe 3, Pe 4 and Pe 6 peptides were too short for PCR amplification, while the Pe 1 peptide was larger but it had three ill-defined residues.

The nucleotide sequence of the primers (23 mer each) was deduced from the N-terminal and C-terminal amino acid sequences of Pe 5 (see FIG. 1b). Since the Pe 5 peptide was produced by CNBr cleavage, a methionine was included at the N terminus to increase the length of the peptide to 24 residues. Bases were chosen according to the codon preference described by R. Lathe in *J. Mol. Biol.*, 183, 111 (1985), the contents of which are incorporated herein by reference; and deoxyinosine (I) was incorporated at the position where degeneracy exceeded more than three fold except towards the 3' end.

Two generated primers for amino acids at the N-terminal (primer A) and amino acids at the C-terminal (primer B) were chemically synthesized and used to amplify the coding sequence of Pe 5 peptide from pooled human bone marrow mRNA of Fy(a–b+) individuals. Primer A (sense) was specific for residues 245 to 252 (see FIG. 1b and SEQ ID NO:1) and consisted of 12 fold degeneracy 5'-ATGAAXATYXTITGGGCITGGTT (where I=deoxyinosine; X=C or,T; and Y=C, T or A). Primer B (antisense) was specific for residues 261–268 (see FIG. 1b and SEQ ID NO:1) and consisted of 32 fold degeneracy 5'-ACIAGMAAMTCIAGICCIAMNAC (where I=deoxyinosine; M=A or G; and N=G, A, T or C).

First strand cDNA was synthesized from Fy(a–b+) phenotype mRNA using the preamplification kit from BRL (Bethesda, Md.) and oligo dT as primer. For enzymatic amplification, cDNA, Primer A, Primer B and Taq polymerase (Stratagene) were incubated in a Perkin-Elmer thermal DNA cycler. The amplification product of expected size (72 bp) was subcloned in pBlueScript-SK vector (Stratagene). The deduced amino acid sequence of the insert, matched the sequence of Pe 5 peptide (see FIG. 1b). From the sequence and ending with WPH of peptide Pe 5 (see FIG. 16) starting with the amino acid residues WFI, the oligonucleotide TGGTTTATTTTCTGGTGGCCTCAT (SEQ ID No: 16) was chemically synthesized, $^{32}$P labeled at the 5' end with T4 polynucleotide kinase (New England Biolabs), and used as a probe to screen a human bone marrow cDNA library (see below). The 24 mer oligonucleotide probe having codon usage for amino acids 251 to 258, successfully identified true gpD protein cDNA clones.

Example 3

Human mRNA and DNA isolation

Poly(A)+ RNA was isolated as follows: Human bone marrow aspirates were washed and cells were lysed in a solution of 5% beta-mercapoethanol plus 6M guanidine thiocyanate, 25 mM sodium citrate (pH 7.0), 50 mM ethylenediaminetetraacetic acid (EDTA) so that the final guanidine concentration became 5M. The solution was passed through a 25 G hypoderminc needle to shear DNA and Sarkosyl was added to 2%. The solution was spun on a 5.7M CsCl, 50 mM EDTA (pH 7.0) cushion in a SW 41 rotor at 32K rpm at 20° C. for 18 hours. The pellet was washed with 6M guanidine hydrochloride and finally with absolute ethanol cooled in dry ice. The pellet was resuspended in diethylpyrocarbonate treated water, adjusted to 0.3M sodium acetate (ph 5.2) and ethanol precipitated. The pellet was resuspended in proteinase K digestion buffer and digested for 2 hours at 37° C., phenol-chloroform extracted and ethanol precipitated. The pellet was then dissolved in water, adjusted to 1×DNase digestion buffer and treated with RNase free DNase (BRL). PolyA+ RNA was isolated with mRNA isolation kit FAST TRACK™ for hydrogen according to the manufacturer's protocol. mRNA from white adult liver, spleen, kidney, brain and fetal liver, as well as erythroleukemia cells K562 were obtained from CLONTECH LABORATORIES. DNA was obtained from peripheral blood white cells of the four Duffy phenotypes by lysing the red blood cells in a whole blood unit with 0.83% $NH_4Cl$ pH 7.4 followed by the standard DNA extraction procedure described by T. Maniatis, E. F. Fritsch, and J. Sambrook, *Molecular Cloning: A Laboratory Manual* (Cold Spring Harbor Lab., Cold Spring Harbor, N.Y.) (1982), the entire contents of which are hereby incorporated by reference.

Example 4

Nucleotide Sequence of the gpD Protein cDNA Clones

A non-amplified human bone marrow cDNA library constructed from pooled mRNA of Fy(a–b+) individuals, was screened with the 24 mer probe. Of $1.9 \times 10^6$ recombinant λZAP II™ phage, four positive clones were selected and sequenced. All clones had overlapping sequences but did not fully extend gpD cDNA. Fyb81 of 1085 bp, which was the only clone that included the ultimate 5' end, and Fyb71 of 1083 bp that extended from nucleotide position 185 to the poly(A)+ tail, were the longest. Fyb31 of 989 bp and Fyb82 of 726 bp extended from nucleotide positions 275 and 527 respectively to the poly(A) tail. Combination of Fyb81 with any other clone, generated the full-length cDNA of gpD protein. FIG. 1a shows the overlapping and the combination of the two longest clones.

The joined Fyb71–81 clone predicted an open reading frame that started at position 176 and stopped at position 1192 encoding a polypeptide of 339 amino acid residues (FIG. 1b). A GenBank™ sequence search (release 77) at the NCBI using the BLAST™ network service, yielded a significant protein sequence homology to human and rabbit interleukin-8 receptors and quasi-total nucleotide sequence homology with a human hippocampus cDNA clone HHCMF86 (see below). The extended product of an antisense primer (from position 57 to 80, FIG. 1b), yielded a sequence of 80 nucleotides which matched exactly with the predicted size at the 5' end of the Fyb81 done (not shown). At positions 176–178, the initiation codon is not embedded within a sequence context most frequently associated with mammalian translation initiation. See M. Kozak, *Nucleic Acids Res.*, 87, 8125 (1987). It was assumed, however, that it is the true initiation codon for the following reasons: (i) it is the only ATG codon at the 5' end; and (ii) from the first methionine residue, the polypeptide encoded by the combined clones, has the same molecular mass as that of de-glycosylated gpD protein. See, A. Chaudhuri and A. O. Pogo (in press) in *Blood Cell Biochemistry*, eds. J. P. Cartron and P. Rouger. (Plenum Press, New York) Vol. 6. At the 3' end, clone Fyb71–81 included the consensus poly(A) addition signal AATTAAA (FIG. 1b and SEQ ID NO:1).

Both clones had a perfect nucleotide sequence match except at the 5' end where several base substitutions yielded six different amino acid predictions. These discrepancies were not a sequencing error, since both DNA strands were sequenced several times. They were a consequence of protein heterogeneity, since the cDNA library was constructed from the mRNA of several Fy(a–b+) individuals.

To establish that Fyb71–81 had a coding sequence specific to gpD protein, the translated sequence was compared with the partial amino acid sequence data obtained from the six peptides Pe 1–Pe 6 (see FIG. 1b). Portions of the predicted amino acid sequence matched with Pe 1 peptide sequenced by the OPA reagent, with four peptides isolated by reverse-phase HPLC (Pe 2, Pe 3, Pe 4 and Pe 6 peptides), and with the Pe 5 peptide isolated by SDS-PAGE. However, two of a total of 62 residues did not match. Thus, the residues at positions 92 and 327 were tryptophan by codon sequence analysis, but they were isoleucine and argirdne, respectively, by amino sequence determination. Since tryptophan is a very unstable residue, the discrepancies may be a technical problem in amino acid sequence analysis. On the other hand, they may be due to the heterogeneity of the gpD protein.

Figure 3A:
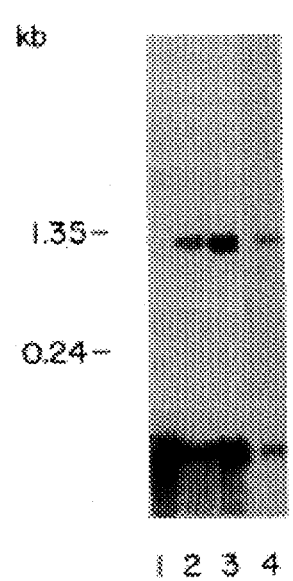
FIG. 3 is Northern (FIG. 3a) and Southern blots (FIG. 3b) probed with either the Fyb71 or Fyb81 insert.

Additional evidence that Fyb71–81 encoded gpD protein, was provided by Northern blot and ELISA analysis. Fyb81 did not detect any mRNA in Duffy negative individuals, but it detected a ~1.27 kilobase (kb) transcript representing the full-length of gpD mRNA in Duffy positive individuals (FIG. 3a). Anti-Fy6 antibody reacted with a 35 mer synthetic peptide (residues 9 to 44, see FIG. 1b), predicted by the Fyb71–81 clone (not shown). The absence of gpD protein specific mRNA in Fy(a–b–) phenotypes (see below) and the reaction of anti-Fy6 with a peptide derived from a gpD cDNA, are strong indications that the clones that were isolated are true Duffy clones.

Example 5

Amino Acid Sequence and Membrane Topology of gpD Protein

The predicted translation product of the Fyb71–81 clone, is an acidic protein of isoelectric point 5.65 and molecular mass $M_r$ 35,733. The protein carries at the amino terminal only two potential canonical sequences for N-glycosylation to asparagine residues. See R. D. Marshall *Annu. Rev. Biochem.*, 41; 673 (1972). This agrees with previous investigations that N-glycosidase F digestion increases gpD mobility on SDS-PAGE and with the chemical detection of N-acetylglucosamine. See A. Chaudhuri and A. O. Pogo, supra; M. J. A. Tanner, D. J. Anstee, G. Mallison, K. Ridgwell, P. G. Martin, N. D. Aventi, and S. F. Parsons, *Carbohydr. Res.*, 178, 203 (1988); and K. Wasniowaska, P. Eichenberger, F. Kugele; and T. J. Hadley, *Biochem. Biophy. Res. Commun.*, 192, 366 (1993).

Figure 2A:
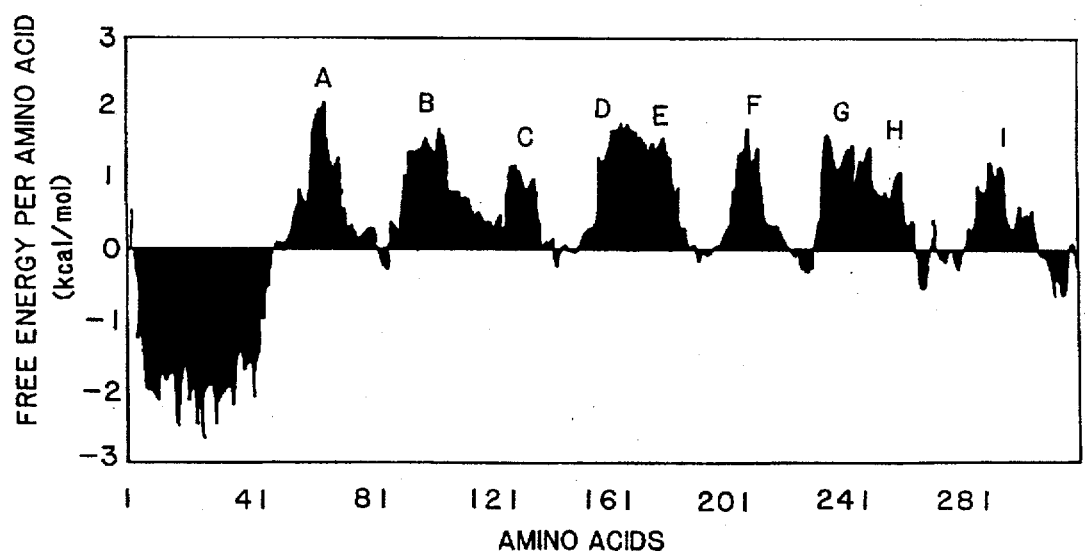
FIG. 2a is a hydropathy plot of the gpD protein sequence.
Figure 2B:
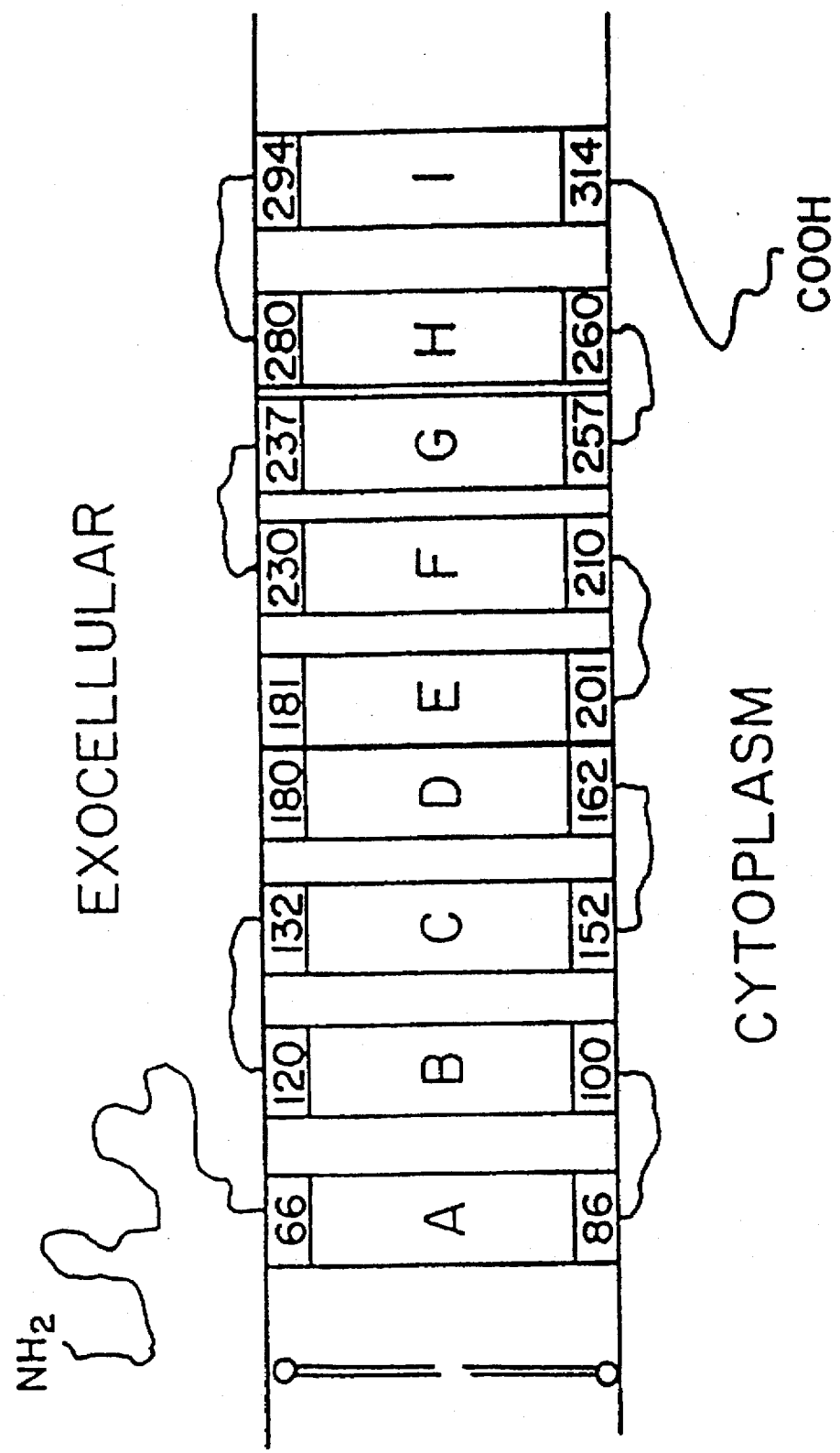
FIG. 2b is a proposed model for the membrane orientation of the gpD protein.

Predictions of transmembrane helices locations from sequence data using the hydropathy map of Engelman et al. (*Ann. Rev. Biophys. Chem.*, 15, 321 (1986)) and a scanning window of 20 residues show that the bulk of the protein is embedded in the membrane (FIG. 2). Nine transmembrane α-helices, a hydrophilic domain of 66 residues at the N-terminus, a hydrophilic domain of 25 residues at the C terminus, and short protruding hydrophilic connecting segments, were predicted. The pair of helices, D and E, is so closely spaced that they may be arranged as coupled antiparallel helices. A schematic illustration of gpD protein topology, is shown in FIG. 2.

The charge-difference rule proposed by Hartmann et al. (*Proc. Natl. Acad. Sci. USA*, 86, 5786 (1989)), predicts that the N terminus is on the exocellular side and the C terminus of the protein is on the cytoplasmic side of the membrane. The N-terminal prediction is validated by the finding of the two potential N-glycosylation sites on the N-terminus. Moreover, the reaction of anti-Fy6 with a synthetic peptide deduced from this domain, establishes its exocellular location experimentally since the antibody binds to erythrocytes. The signal-anchor sequence for membrane insertion probably lies in the first transmembrane α-helix that follows the N-terminal domain. See H. P. Wessels and M. Spies, *Cell*, 55, 61 (1988); and G. Blobel, *Proc. Natl. Acad. Sci. USA*, 77, 1496 (1980). From there on, the protein is deeply buried in the membrane and exists at residue 314 on the cytoplasmic side of the membrane (FIG. 2). The topological predictions of helices, hydrophilic connecting segments and the location of the C-terminal fragment, should be substantiated by direct biochemical and immunochemical analysis.

Duffy gpD protein is deeply buried in the membrane like the membrane-associated fragment of Band 3 (see D. Jay, *Annu. Rev. Biochem.*, 55, 511 (1986)), the human blood group Rh polypeptide (see, B. Chérif-Zahar et al., *Proc. Natl. Acad. Sci. USA*, 87, 6243 (1990); and N. D. Avent et al., *Biochem. J.*, 271, 821 (1990)), bacteriorhodopsin (see P. Carlton et al., *EMBO J.*, 4, 1593 (1985)), and lipophilin (see W. Stoffel et al., *Hoppe-Seyler' Z. Physiol. Chem.*, 364, 1455 (1983)). The significant homology of gpD protein with interleukin-8 receptors is very intriguing. See W. E. Holmes et al., *Science*, 253, 1278 (1991); and P. M. Murphy et al., *Science*, 253, 1280 (1991). If dpD protein bind chemokines and has the ability to activate a signal transduction cascade, this gives rise to gpD protein as a new class of proinflammatory mediators. Thus, gpD protein is not present in white blood cells, since a rabbit polyclonal antibody (anti-gpD) against purified and denatured gpD protein that reacts with erythrocytes and their precursors does not react with any white blood cells (unpublished results).

Example 6

RNA Blot Analysis (Northern)

Poly(A)+ RNAs were run on formaldehyde/agarose gel and transferred onto Hybond™ N+ nylon membranes (Amersham Corp.). They were hybridized in QuickHyb™ (Stratagene) and washed according to the manufacturer's instructions.

On Northern blot analysis Fyb71 or Fyb81 clone detected a ~1.27 kb mRNA species in the bone marrow of the three Duffy positive phenotypes but not in individuals of Fy(a–b–) phenotype (FIG. 3a). The absence of gpD mRNA was consistent with the absence of gpD protein in Duffy negative individuals. Anti-gpD antibody did not react with any red cell membrane protein of Fy(a–b–) erythrocytes (not shown). Duffy negative individuals did not express gpD protein, because they do not synthesize Duffy specific mRNA.

In FIG. 3a, lane 1 contained 10 μg of Fy(a–b–) mRNA, lanes 2 and 3 contained 5 μg of Fy(a+b–) mRNA and Ry(a–b+) mRNA respectively, and lane 4 contained 2 μg of Fy(a+b+) mRNA. They were resolved on a 2% denaturing agarose gel, blotted, hybridized, and autoradiographed for 72 h at –80° C. RNA size markers shown: human 28S (5.1 kb) and 18S (2.0 kb) rRNA, and the 1.35 kb GIBCOBRL marker (LIFE TECHNOLOGIES), were used to calculate the size of gpD mRNA. The actin probe as the bottom was used as control of sample loading. RNA integrity was indicated by the presence of the two rRNA in the poly(A)+ fraction and the actin probe.

Example 7

DNA Blot Analysis (Southern)

All restriction enzyme digestions were performed according to the conditions suggested by the supplier (New England Biolabs). Digested DNA was size-fractionated on 0.8% agarose gel and blotted as described for Northern analysis. Hybridization in QuickHyb™ solution was carried out at 68° C. for 1 hour according to the manufacturer's instructions.

Figure 3B:
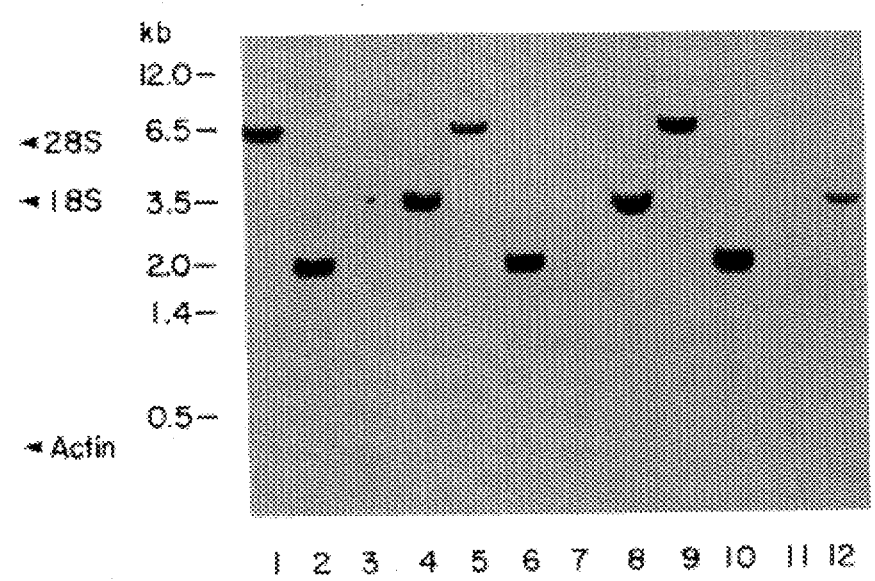

On Southern blot analysis Fyb71 or Fyb81 probe hybridized with DNA of Duffy positive and negative individuals (FIG. 3b). They identified a single band of 6.5 kb in Bam HI, two bands of 12 kb and 2 kb in EcoRI, and two bands of 3.5 kb and 1.4 kb in Pst I digested DNA. These findings agree with the restriction map of the Fyb71 and Fyb 81 clones and show a single copy gene. Determination of the structural differences among the genes of Duffy positive and negative individuals, should clarify the mechanism of gpD gene repression in negative individuals. A functional silencer element described in other systems may selectively repress transcription of gpD gene in the erythrocytes of Fy(a–b–) individuals. See L. Li, T. Suzuki, N. Mori, and P. Greengard, *Proc. Natl. Acad. Sci. USA*, 90, 1460 (1993). The Duffy system is different from the ABO (F. Yamamoto et al., *Nature*, 345, 229 (1990)) and Kell systems where mRNA has been found in individuals who do not express the blood group determinants.

In FIG. 3b, each lane contained 10 µg of digested DNA; lanes 1–4 contained Fy(a–b–), lanes 5–8 contained Fy(a+b–), and lanes 9 to 12 contained Fy(a–b+) DNA. The enzyme digestions were as follows: lanes 1, 5 and 9 Bam H1; lanes 2, 6 and 10 Eco R1; lanes 3, 7 and 11 Hinf1; and lanes 4, 8 and 12 Pst 1. They were resolved on 0.8% agarose gel, blotted, hybridized, and autoradiographed for seven days at –80° C. Sizes were calculated from the positions of the GIBCOBRL DNA markers.

Figure 4:
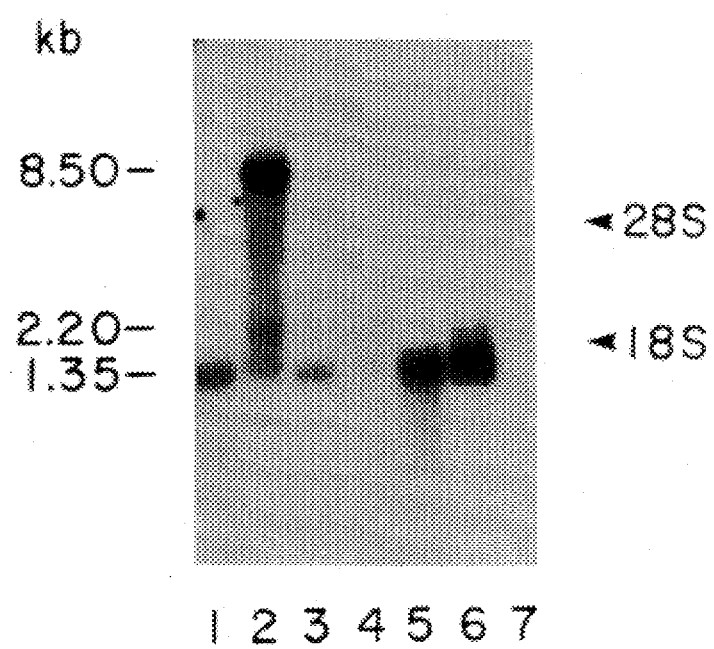
FIG. 4 is a Northern blot analysis of poly(A)+ RNA obtained from human tissues probed with the insert of Fyb81 clone.

As indicated in FIG. 4, a 1.27 kb mRNA species was found in adult spleen and kidney, fetal liver but not in adult liver and K562 erythroleukemia cells. Hybridization with the β-globin probe showed a strong signal in bone marrow and fetal liver; it showed a weak signal in adult spleen but no signal in adult liver, brain and kidney (not shown). The presence of gpD mRNA in fetal liver was expected since the fetal liver is an erythropoietic organ. In human brain, a strong band of 8.5 kb and a faint band of 2.2 kb were detected. This bears some interesting possibilities. It indicates that in brain, there is a Duffy related protein. Also, this idea is supported by the quasi-total homology between Fyb71-81 clone and a human hippocampus cDNA clone HHCMF86, which was recently identified (see M. D. Adams et al., *Nature*, 355, 632 (1992)) and is designated SEQ ID No: 15. However, it is unlikely that the 8.5 kb brain mRNA codes for a Duffy protein with long 5' and 3' untranslated sequences. It is possible that the brain mRNA codes for a larger protein which has extensive homology with gpD protein. The homologies of these mRNA species with gpD specific mRNA, remain to be demonstrated by sequence analysis; however, the findings strongly indicate that gpD protein or a similar protein is produced in kidney, non-hemopoietic spleen cells, and probably in brain.

A chart showing the DNA sequence homology between gpD protein and human hippocampus cDNA clone HHCMF86 is presented as FIG. 5. The HHCMF86 cDNA clone was obtained from a 2 year old Caucasian female (Adams et al., *Nature*, 355, 632 (1992)). There are several undefined bases in HHCMF86 and the two clones have the same ORF up to position 623 in gpD protein (290 in HHCMF86). HHCMF86 has an extra adenine after this position producing a frame shift in the ORF. It is likely that the extra adenine may be a sequence error in HHCMF86 cDNA.

In FIG. 4, lanes 1, 3, 5 and 7 contained 2 µg of Fy(a–b+) bone marrow, fetal liver, adult spleen and erythroleukemia (K562) mRNAs respectively. Lanes 2, 4 and 6 contained 7 µg of total brain, adult liver, and adult kidney mRNA, respectively. They were resolved on a 1.5% denaturing agarose gel and autoradiographed for five days at –80° C.

Example 8

Construction and Screening of a cDNA Human Bone Marrow Library

A mixture of mRNA of several Fy(a–b+) individuals, the BRL Superscript Choice™ System and oligo dT as a primer, were used to prepare cDNA. The cDNA was ligated into λZAP II™ vector and packaged with Gigapack Gold™ (Stratagene) extract. About $1.9 \times 10^6$ unamplified cDNA clones were screened with the $^{32}$P-labeled probe described above. cDNA inserts into pBluescript were isolated by the plasmid rescue method according to manufacturer's protocol. Both DNA strands were sequenced using vector primers; and primers were designed from the sequenced regions of the transcript.

Example 9

Primer Extension

A $^{32}$P-labeled 24-mer antisense primer from nucleotides 57 to 80 of the coding strand (FIG. 1b) was extended on Fy(a–b+) mRNA using the Preamplification Kit (BRL) and the products were separated on a 6% sequencing gel. The M13 sequence ladder was used to determine sizes of products.

It will be appreciated that the instant specification and claims are set forth by way of illustration and not limitation, and that various modifications and changes may be made without departing from the spirit and scope of the present invention.

What is claimed is:

1. A peptide consisting of the amino acid sequence of a continuous fragment of gpD protein, said continuous fragment consisting of less than the entire amino acid sequence of gpD protein and said continuous fragment comprising the amino acid sequence depicted in SEQ ID No: 14.

2. A peptide according to claim 1, consisting of the amino acid sequence depicted in SEQ ID No: 8 or of the amino acid sequence of a continuous fragment thereof which also comprises the amino acid sequence depicted in SEQ ID No: 14.

3. The peptide according to claim 2, consisting of the amino acid sequence depicted in SEQ ID No: 8.

4. The peptide according to claim 1, consisting of the amino acid sequence depicted in SEQ ID No: 9.

5. The peptide according to claim 1, consisting of the amino acid sequence depicted in SEQ ID No: 10.

6. The peptide according to claim 1, consisting of the amino acid sequence depicted in SEQ ID No: 14.

7. A composition useful to reduce the severity of *P. vivax* infection in a warm-blooded animal suffering therefrom comprising an amount effective therefor of a peptide according to claim 1 in admixture with a physiologically acceptable diluent.

8. The composition according to claim 7, wherein the peptide consists of the amino acid sequence depicted in SEQ ID No: 8 or of the amino acid sequence of a continuous fragment thereof which also comprises the amino acid sequence depicted in SEQ ID No: 14.

9. The composition according to claim 8, wherein the peptide consists of the amino acid sequence depicted in SEQ ID No: 8.

10. The composition according to claim 7, wherein the peptide consists of the amino acid sequence depicted in SEQ ID No: 9.

11. The composition according to claim 7, wherein the peptide consists of the amino acid sequence depicted in SEQ ID No: 10.

12. The composition according to claim 7, wherein the peptide consists of the amino acid sequence depicted in SEQ ID No: 14.

13. A method of reducing the severity of *P. vivax* infection in a warm-blooded animal suffering therefrom comprising administering to said animal an effective mount therefor of a peptide according to claim 1.

14. The method according to claim 13, wherein the peptide consists of the amino acid sequence depicted in SEQ ID No:8 or of the amino acid sequence of a continuous fragment thereof which also comprises the amino acids sequence depicted in SEQ ID No: 14.

15. The method according to claim 13, wherein the peptide consists of the amino acid sequence depicted in SEQ ID No: 9.

16. The method according to claim 13, wherein the peptide consists of the amino acid sequence depicted in SEQ ID No: 10.

17. The method according to claim 13, wherein the peptide consists of the amino acid sequence depicted in SEQ ID No: 14.

18. The method according to claim 14, wherein the peptide consists of the amino acid sequence depicted in SEQ ID No: 8.

* * * * *

UNITED STATES PATENT AND TRADEMARK OFFICE
CERTIFICATE OF CORRECTION

PATENT NO. : 5,683,696
DATED : November 4, 1997
INVENTOR(S) : Pogo, et al.

It is certified that error appears in the above-identified patent and that said Letters Patent is hereby corrected as shown below:

Col. 25, line 1  Delete " mount " and substitute -- amount --

Signed and Sealed this

Twenty-ninth Day of February, 2000

Attest:

Attesting Officer

Q. TODD DICKINSON

Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
( A ) LENGTH: 1267 nucleotides
( B ) TYPE: nucleic acid ( C ) STRANDEDNESS: double
( D ) TOPOLOGY: linear ( x i ) SEQUENCE DESCRIPTION: SEQ ID NO: 1:

```
GGCTTCCCCA  GGACTGTTCC  TGCTCCGGCT  CTTCAGGCTC                    40

CCTGCTTTGT  CCTTTTCCAC  TGTCCGCACT  GCATCTGACT                    80

CCTGCAGAGA  CCTTGTTCTC  CCACCCGACC  TTCCTCTCTG                   120

TCCTCCCCTC  CCACCTGCCC  CTCAGTTCCC  AGGAGACTCT                   160

TCCGGTGTAA  CTCTG ATG GCC TCC TCT GGG TAT GTC CTC                199
                  Met Ala Ser Ser Gly Tyr Val Leu
                   1               5

CAG GCG GAG CTC TCC CCC TCA ACT GAG AAC TCA AGT CAG              238
Gln Ala Glu Leu Ser Pro Ser Thr Glu Asn Ser Ser Gln
        10              15              20

CTG GAC TTC GAA GAT GTA TGG AAT TCT TCC TAT GGT GTG              277
Leu Asp Phe Glu Asp Val Trp Asn Ser Ser Tyr Gly Val
                25              30

AAT GAT TCC TTC CCA GAT GGA GAC TAT GAT GCC AAC CTG              316
Asn Asp Ser Phe Pro Asp Gly Asp Tyr Asp Ala Asn Leu
35              40              45

GAA GCA GCT GCC CCC TGC CAC TCC TGT AAC CTG CTG GAT              355
Glu Ala Ala Ala Pro Cys His Ser Cys Asn Leu Leu Asp
            50              55                  60

GAC TCT GCA CTG CCC TTC TTC ATC CTC ACC AGT GTC CTG              394
Asp Ser Ala Leu Pro Phe Phe Ile Leu Thr Ser Val Leu
                65              70

GGT ATC CTA GCT AGC AGC ACT GTC CTC TTC ATG CTT TTC              433
Gly Ile Leu Ala Ser Ser Thr Val Leu Phe Met Leu Phe
        75              80              85

AGA CCT CTC TTC CGC TGG CAG CTC TGC CCT GGC TGG CCT              472
Arg Pro Leu Phe Arg Trp Gln Leu Cys Pro Gly Trp Pro
                90              95

GTC CTG GCA CAG CTG GCT GTG GGC AGT GCC CTC TTC AGC              511
Val Leu Ala Gln Leu Ala Val Gly Ser Ala Leu Phe Ser
100             105             110

ATT GTG GTG CCC GTC TTG GCC CCA GGG CTA GGT AGC ACT              550
Ile Val Val Pro Val Leu Ala Pro Gly Leu Gly Ser Thr
        115             120             125

CGC AGC TCT GCC CTG TGT AGC CTG GGC TAC TGT GTC TGG              589
Arg Ser Ser Ala Leu Cys Ser Leu Gly Tyr Cys Val Trp
                130             135

TAT GGC TCA GCC TTT GCC CAG GCT TTG CTG CTA GGG TGC              628
Tyr Gly Ser Ala Phe Ala Gln Ala Leu Leu Leu Gly Cys
        140             145             150

CAT GCC TCC CTG GGC CAC AGA CTG GGT GCA GGC CAG GTC              667
Asn Ala Ser Leu Gly Asn Arg Leu Gly Ala Gly Gln Val
                155             160

CCA GGC CTC ACC CTG GGG CTC ACT GTG GGA ATT TGG GGA              706
Pro Gly Leu Thr Leu Gly Leu Thr Val Gly Ile Trp Gly
165             170             175

GTG GCT GCC CTA CTG ACA CTG CCT GTC ACC CTG GCC AGT              745
Val Ala Ala Leu Leu Thr Leu Pro Val Thr Leu Ala Ser
        180             185             190

GGT GCT TCT GGT GGA CTC TGC ACC CTG ATA TAC AGC ACG              784
Gly Ala Ser Gly Gly Leu Cys Thr Leu Ile Tyr Ser Thr
                195             200

GAG CTG AAG GCT TTG CAG GCC ACA CAC ACT GTA GCC TGT              823
Lys Leu Lys Ala Leu Gln Ala Thr Asn Thr Val Ala Cys
205             210             215
```

| | | | | | | | | | | | | |
|---|---|---|---|---|---|---|---|---|---|---|---|---|
| CTT | GCC | ATC | TTT | GTC | TTG | TTG | CCA | TTG | GGT | TTG | TTT | GGA | 862
| Leu | Ala | Ile | Phe | Val | Leu | Leu | Pro | Leu | Gly | Leu | Phe | Gly |
| | | 220 | | | | | 225 | | | | | |

```
CTT GCC ATC TTT GTC TTG TTG CCA TTG GGT TTG TTT GGA          862
Leu Ala Ile Phe Val Leu Leu Pro Leu Gly Leu Phe Gly
        220                 225

GCC AAG GGG CTG AAG AAG GCA TTG GGT ATG GGG CCA GGC          901
Ala Lys Gly Leu Lys Lys Ala Leu Gly Met Gly Pro Gly
230             235                 240

CCC TGG ATG AAT ATC CTG TGG GCC TGG TTT ATT TTC TGG          940
Pro Trp Met Asn Ile Leu Trp Ala Trp Phe Ile Phe Trp
        245                 250                 255

TGG CCT CAT GGG GTG GTT CTA GGA CTG GAT TTC CTG GTG          979
Trp Pro Asn Gly Val Val Leu Gly Leu Asp Phe Leu Val
            260                 265

AGG TCC AAG CTG TTG CTG TTG TCA ACA TGT CTG GCC CAG         1018
Arg Ser Lys Leu Leu Leu Leu Ser Thr Cys Leu Ala Gln
    270                 275                 280

CAG GCT CTG GAC CTG CTG CTG AAC CTG GCA GAA GCC CTG         1057
Gln Ala Leu Asp Leu Leu Leu Met Leu Ala Glu Ala Leu
                285                 290

GCA ATT TTG CAC TGT GTG GCT ACG CCC CTG CTC CTC GCC         1096
Ala Ile Leu Asn Cys Val Ala Thr Pro Leu Leu Leu Ala
295                     300                 305

CTA TTC TGC CAC CAG GCC ACC CGC ACC CTC TTG CCC TCT         1135
Leu Phe Cys Lys Gln Ala Thr Arg Thr Leu Leu Pro Ser
        310                 315                 320

CTG CCC CTC CCT GAA GGA TGG TCT TCT CAT CTG GAC ACC         1174
Leu Pro Leu Pro Glu Gly Trp Ser Ser Asn Leu Asp Thr
                325                 330

CTT GGA AGC AAA TCC TAGTTCTCTT CCCACCTGTC AACCTGAATT        1219
Leu Gly Ser Lys Ser
        335

AAAGTCTACA CTGCCTTTGT GAAAAAAAAA AAAAAAAAA               1259

AAAAAAA                                                     1267
```

( 2 ) INFORMATION FOR SEQ ID NO: 2:

( i ) SEQUENCE CHARACTERISTICS:
       ( A ) LENGTH: 48 nucleotides
       ( B ) TYPE: nucleic acid
       ( C ) STRANDEDNESS: single
       ( D ) TOPOLOGY: linear ( x i ) SEQUENCE DESCRIPTION: SEQ ID NO: 2:

```
CCTCTCTTCC GCTGGCAGCT CTGCCCTGGC TGGCCTGTCC                  40

TGGCACAG                                                     48
```

( 2 ) INFORMATION FOR SEQ ID NO: 3:

( i ) SEQUENCE CHARACTERISTICS:
       ( A ) LENGTH: 15 nucleotides
       ( B ) TYPE: nucleic acid
       ( C ) STRANDEDNESS: single
       ( D ) TOPOLOGY: linear ( x i ) SEQUENCE DESCRIPTION: SEQ ID NO: 3:

```
TTCAGCATTG TGGTG                                             15
```

( 2 ) INFORMATION FOR SEQ ID NO: 4:

( i ) SEQUENCE CHARACTERISTICS:
       ( A ) LENGTH: 15 nucleotides
       ( B ) TYPE: nucleic acid
       ( C ) STRANDEDNESS: single ( D ) TOPOLOGY: linear ( x i ) SEQUENCE DESCRIPTION: SEQ ID NO: 4:

TTTGCCCAGG CTTTG        15

( 2 ) INFORMATION FOR SEQ ID NO: 5:

( i ) SEQUENCE CHARACTERISTICS:
        ( A ) LENGTH: 9 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GTGGGAATT        9

( 2 ) INFORMATION FOR SEQ ID NO: 6:

( i ) SEQUENCE CHARACTERISTICS:
        ( A ) LENGTH: 72 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

ATGAATATCC TGTGGGCCTG GTTTATTTTC TGGTGGCCTC        40

CTCATGGGGT TCTAGGACTG GATTTCCTGG TG        72

( 2 ) INFORMATION FOR SEQ ID NO: 7:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CCCTCTCTGC CCCTCCCTGA AGGATGG        27

( 2 ) INFORMATION FOR SEQ ID NO: 8:

( i ) SEQUENCE CHARACTERISTICS:
        ( A ) LENGTH: 66 amino acids
        ( B ) TYPE: amino acid
        ( D ) TOPOLOGY: linear ( x i ) SEQUENCE DESCRIPTION: SEQ ID NO: 8:

Met Ala Ser Ser Gly Tyr Val Leu Gln Ala Glu Leu Ser Pro Ser
             5                    10                  15

Thr Glu Asn Ser Ser Gln Leu Asp Phe Glu Asp Val Trp Asn Ser
            20                    25                  30

Ser Tyr Gly Val Asn Asp Ser Phe Pro Asp Gly Asp Tyr Asp Ala
            35                    40                  45

Asn Leu Glu Ala Ala Ala Pro Cys His Ser Cys Asn Leu Leu Asp
            50                    55                  60

Asp Ser Ala Leu Pro Phe
            65

( 2 ) INFORMATION FOR SEQ ID NO: 9:

( i ) SEQUENCE CHARACTERISTICS:
        ( A ) LENGTH: 44 amino acids
        ( B ) TYPE: amino acid
        ( D ) TOPOLOGY: linear -continued ( x i ) SEQUENCE DESCRIPTION: SEQ ID NO: 9:

Met Ala Ser Ser Gly Tyr Val Leu Gln Ala Glu Leu Ser Pro Ser
                5                   10                  15

Thr Glu Asn Ser Ser Gln Leu Asp Phe Glu Asp Val Trp Asn Ser
                20                  25                  30

Ser Tyr Gly Val Asn Asp Ser Phe Pro Asp Gly Asp Tyr Asp
                35                  40

( 2 ) INFORMATION FOR SEQ ID NO: 10:

( i ) SEQUENCE CHARACTERISTICS:
        ( A ) LENGTH: 35 amino acids
        ( B ) TYPE: amino acid
        ( D ) TOPOLOGY: linear ( x i ) SEQUENCE DESCRIPTION: SEQ ID NO: 10:

Ala Glu Leu Ser Pro Ser Thr Glu Asn Ser Ser Gln Leu Asp Phe
                5                   10                  15

Glu Asp Val Trp Asn Ser Ser Tyr Gly Val Asn Asp Ser Phe Pro
                20                  25                  30

Asp Gly Asp Tyr Asp
                35

( 2 ) INFORMATION FOR SEQ ID NO: 11:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO: 11:

Asp Phe Glu Asp Val Trp Asn Ser Ser Tyr Gly Val Asn Asp Ser
                5                   10                  15

Phe Pro Asp Gly Asp Tyr Asp
                20

( 2 ) INFORMATION FOR SEQ ID NO: 12:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO: 12:

Ala Asn Leu Glu Ala Ala Ala Pro Cys His Ser Cys Asn Leu Leu
                5                   10                  15

Asp Asp Ser Ala Leu Pro Phe
                20

( 2 ) INFORMATION FOR SEQ ID NO: 13:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO: 13:

Ala Glu Leu Ser Pro Ser Thr Glu Asn Ser Ser Gln Leu
                5                   10

( 2 ) INFORMATION FOR SEQ ID NO: 14:

( i ) SEQUENCE CHARACTERISTICS:
        ( A ) LENGTH: 22 amino acids (B) TYPE: amino acid
(D) TOPOLOGY: linear (xi) SEQUENCE DESCRIPTION: SEQ ID NO: 14:

Ala Glu Leu Ser Pro Ser Thr Glu Asn Ser Ser Gln Leu Asp Phe
                  5                   10                  15

Glu Asp Val Trp Asn Ser Ser
                20

(2) INFORMATION FOR SEQ ID NO: 15:

(i) SEQUENCE CHARACTERISTICS:
    (A) LENGTH: 328 nucleotides
    (B) TYPE: nucleic acid
    (C) STRANDEDNESS: single
    (D) TOPOLOGY: linear (xi) SEQUENCE DESCRIPTION: SEQ ID NO: 15:

| | | | | |
|---|---|---|---|---|
| CCACTCCTGT | AACCTGCTGG | ATGACTCTGC | ACTGCCCTTC | 40 |
| TTCATCCTCA | CCAGTGTCCT | GGGTATCCTA | GCTAGCAGCA | 80 |
| CTGTCCTCTT | CATGCTTTTN | AGACCTCTCT | TCCGCTGGCA | 120 |
| GCTCTGCCCT | GGCTGGCCTG | TCCTGGCACA | GCTGGCTGTG | 160 |
| GGCAGTGCCC | TCTTCAGCAT | TGTGGTGCCC | GTTTTGGCCC | 200 |
| CAGGGCTAGG | TAGCACTCGC | AGCTCTGCCC | TGTGTAGCCT | 240 |
| GGGCTACTGT | GTCTGGTATG | GCTCAGCCTT | TGNCCAGGCT | 280 |
| TTGCTGCTAA | GGGTGCCATG | CCTCCCTGGG | NCACAGACTG | 320 |
| GGTGCAGG   |            |            |            | 328 |

(2) INFORMATION FOR SEQ ID NO: 16:

(i) SEQUENCE CHARACTERISTICS:
    (A) LENGTH: 24 nucleotides
    (B) TYPE: nucleic acid
    (C) STRANDEDNESS: single
    (D) TOPOLOGY: linear (xi) SEQUENCE DESCRIPTION: SEQ ID NO: 16:

TGGTTTATTT TCTGGTGGCC TCAT                                24